(12) United States Patent
Bargach et al.

(10) Patent No.: US 7,293,715 B2
(45) Date of Patent: Nov. 13, 2007

(54) MARKING SYSTEM AND METHOD

(75) Inventors: Saad Bargach, Houston, TX (US); Lennox Reid, Houston, TX (US); Soraya S. Betancourt, Ridgefield, CT (US); Oliver C. Mullins, Ridgefield, CT (US); Christopher S. Del Campo, Houston, TX (US); Ashley C. Kishino, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 49 days.

(21) Appl. No.: 11/014,327

(22) Filed: Dec. 16, 2004

(65) Prior Publication Data

US 2006/0131376 A1 Jun. 22, 2006

(51) Int. Cl.
*G06K 19/06* (2006.01)
*G06K 7/00* (2006.01)
*G06F 17/00* (2006.01)

(52) U.S. Cl. .................. 235/492; 235/375; 235/486
(58) Field of Classification Search ............... 235/375, 235/376, 462.01, 492; 455/40, 899; 702/6
See application file for complete search history.

(56) References Cited

U.S. PATENT DOCUMENTS

| | | | |
|---|---|---|---|
| 4,860,581 A | 8/1989 | Zimmerman et al. | |
| 4,911,001 A | 3/1990 | Ferguson | |
| 4,936,139 A | 6/1990 | Zimmerman et al. | |
| 5,109,697 A | 5/1992 | Millheim et al. | |
| 5,134,271 A * | 7/1992 | Sondergeld et al. | 235/376 |
| 5,175,420 A * | 12/1992 | Bianco | 235/462.33 |
| 5,310,013 A | 5/1994 | Kishino et al. | |
| 5,591,974 A * | 1/1997 | Troyer et al. | 250/336.1 |
| 5,803,186 A | 9/1998 | Berger et al. | |
| 5,991,602 A * | 11/1999 | Sturm | 455/40 |
| 6,285,955 B1 * | 9/2001 | Goldwasser | 702/6 |
| 6,333,700 B1 | 12/2001 | Thomeer et al. | |
| 6,404,340 B1 | 6/2002 | Paradiso et al. | |
| 6,597,175 B1 | 7/2003 | Brisco | |
| 6,736,210 B2 * | 5/2004 | Hosie et al. | 166/254.2 |
| 2004/0020645 A1 | 2/2004 | Clark et al. | |
| 2004/0129769 A1* | 7/2004 | Kovach | 235/375 |
| 2004/0140126 A1 | 7/2004 | Hill et al. | |

FOREIGN PATENT DOCUMENTS

| | | |
|---|---|---|
| EP | 1 243 946 A2 | 9/2002 |
| EP | 1 243 946 A3 | 7/2003 |
| WO | WO2005/086699 | 9/2005 |

OTHER PUBLICATIONS

Accenture, Radio Frequency Identification (RFID) white paper (Nov. 16, 2001).
Paradiso, Joseph et al., Swept-Frequency, Magnetically-Coupled Resonant Tages for Realtime, Continuous, Multiparameter Control, MIT Media Laboratory, Presented at the CHI99 Conference, Pittsburgh, PA, Apr. 1999, pp. 1-2.

* cited by examiner

*Primary Examiner*—Thien M. Le
*Assistant Examiner*—April A. Taylor
(74) *Attorney, Agent, or Firm*—Matthias Abrell; Kevin P. McEnaney; Jaime Castano

(57) ABSTRACT

A marking system and method for a well site sample is provided. The system includes a container for collecting the well site sample, a marker applied to the container and a scanner adapted to read the marker. Data may be uploaded to and/or downloaded from the marker.

30 Claims, 3 Drawing Sheets

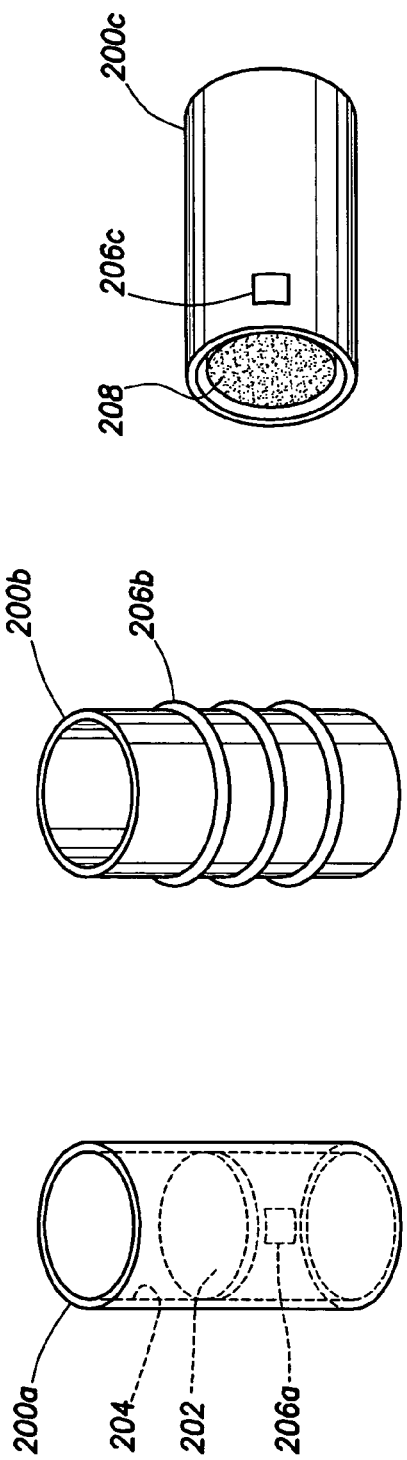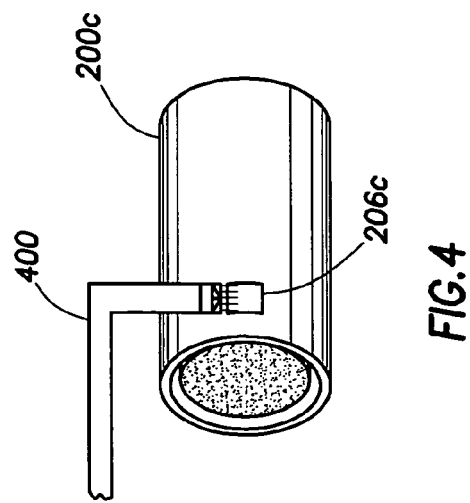

MARKING SYSTEM AND METHOD

BACKGROUND OF THE INVENTION

1. Field of the Invention

The present invention relates to techniques for marking containers for use in wellbore operations. More specifically, the present invention relates to techniques for identification and/or data collection of containers for well site specimens.

2. Background of the Related Art

Wellbores are drilled to locate and produce hydrocarbons. A string of downhole pipes and tools with a drill bit at an end thereof, commonly known in the art as a drill string, is advanced into the ground to form a wellbore penetrating (or targeted to penetrate) a subsurface formation of interest. As the drill string is advanced, a drilling mud is pumped down through the drill string and out the drill bit to cool the drill bit and carry away cuttings and to control downhole pressure. The drilling mud exiting the drill bit flows back up to the surface via the annulus formed between the drill string and the wellbore wall, and is filtered in a surface pit for recirculation through the drill string. The drilling mud is also used to form a mudcake to line the wellbore.

It is often desirable to perform various evaluations of the formations penetrated by the wellbore during drilling operations, such as during periods when actual drilling has temporarily stopped. In some cases, the drill string may be provided with one or more drilling tools to test and/or sample the surrounding formation. In other cases, the drill string may be removed from the wellbore (called a "trip") and one or more wireline tools may be deployed into the wellbore to evaluate the formation. Such drilling tools and wireline tools, as well as other wellbore tools conveyed, for example, on coiled tubing, are also referred to herein simply as "downhole tools." During formation evaluation, including sampling and/or testing, performed by such downhole tools may be used, for example, to locate valuable hydrocarbons and manage the production thereof.

Formation evaluation often requires that fluid samples from the formation be drawn into a downhole tool for testing and/or sampling. Various devices, such as probes and/or packers, are extended from the downhole tool to isolate a region of the wellbore wall, and thereby establish fluid communication with the formation surrounding the wellbore. Fluid may then be drawn into the downhole tool using the probe and/or packer. Examples of a wireline formation evaluation tool are described in U.S. Pat. Nos. 4,860,581 and 4,936,139. Coring tools are also used to drill and remove core samples of the formation. Such core samples may be contained in sleeves. Examples of coring tools and associated sleeves are described in US Patent Application No. 2004/0140126. Formation evaluation may also be performed in some drilling tools provided with such capabilities as described, for example, in U.S. Pat. No. 5,803,186.

Samples taken during wellbore operations are usually collected in containers. For example, formation fluid samples drawn into the downhole tool are collect in sample chambers and retrieved to the surface. Similarly, core samples are sometimes contained in sleeves to protect the integrity of the sample as it is retrieved and transported. Other samples, such as mud, frac fluids, etc., may also be collected at the wellsite. The collected samples are often sent to labs for testing. Presently, samples are either removed individually from a downhole tool and placed in bins that are manually labeled, or that are shipped directly to and removed by a test lab.

Throughout many industries, various techniques have been developed for identifying products. Bar code labels on groceries is an example of an identification system that may be used to mark and identify containers and the items therein. Marking systems have been used in downhole applications, for example, for core samples taken from downhole formations. An example of such a system is described in U.S. Pat. No. 5,310,013.

Despite such advances in marking for various products, there remains a need for a system capable of identifying containers and specimens, such as samples, contained therein as they are used at a wellsite and/or transported to other locations. It is desirable that such a system provide a marker associated with a container for collecting various specimens associated with a wellsite. It is further desirable that the system be capable of providing one or more of the following, among others: a marker adapted to receive data associated with a container and/or its contents; a reader capable of reading the marker at an offsite, downhole and/or surface location; a scanner capable of recording data to the marker; and a processor adapted to manipulate the data associated with the marker.

SUMMARY OF THE INVENTION

In at least one aspect, the present invention relates to a marking system for a well site sample. The system includes at least one container for collecting the well site sample, at least one marker applied to the container and a scanner adapted to read the marker. The marker has an identifier associated therewith.

In another aspect, the invention relates to a method of processing downhole data for a well site sample. The method involves creating at least one marker for at least one container, uploading background data relating to the container to the marker, collecting a well site sample in the at least one container and downloading the data to a surface computer.

Other aspects of the invention may be appreciated from the description provided.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not to be considered limiting of its scope, for the invention may admit to other equally effective embodiments.

FIG. 2A is a container for collecting fluid samples in the downhole tool.

FIG. 2B is a container for collecting specimens at a wellsite.

FIG. 2C is a container for housing a core sample taken by the downhole tool.

FIG. 3 is a schematic diagram of a set of containers having markers applied thereto.

FIG. 4 is a schematic view of a scanner positioned adjacent to the sample chamber of FIG. 2A.

DETAILED DESCRIPTION OF THE INVENTION

Figure 1:
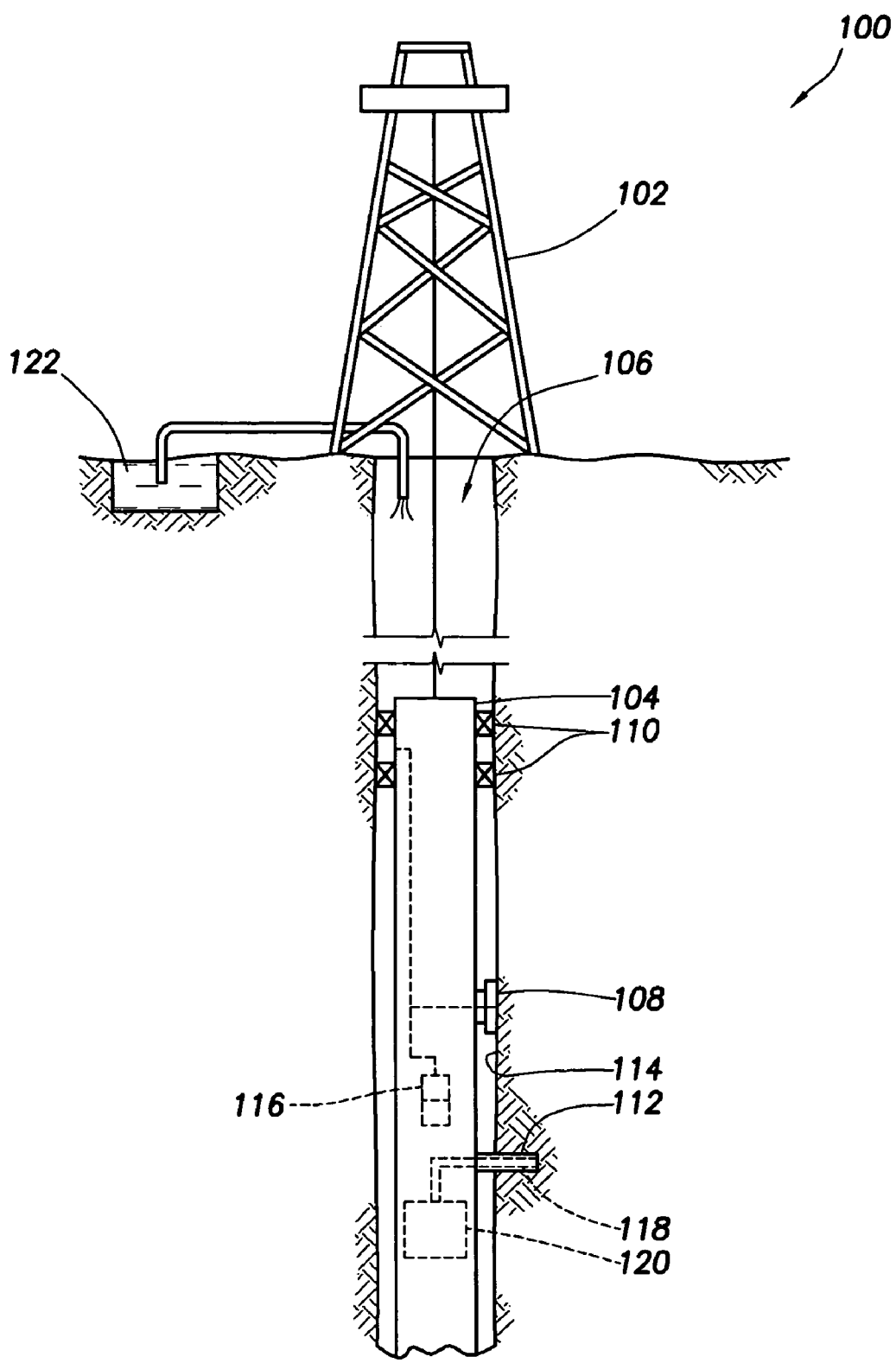
FIG. 1 is a schematic view of a rig having a downhole tool advanced into the earth to form a wellbore.

Presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic in the interest of clarity and conciseness.

Referring now to FIG. 1, a wellbore system 100 is depicted. The wellbore system includes a rig 102 having a downhole tool 104 extending into a bore hole 106. The downhole tool is a wireline tool provided with various components or modules for performing downhole operations, such as coring, testing and sampling. For example, a probe 108 and dual packers 110 are shown for establishing fluid communication between the downhole tool and wellbore and mudcake. Techniques for performing downhole operations, such as sampling and testing, using a probe and/or packer are described in U.S. Pat. Nos. 4,860,581 and 4,936,139, the entire contents of which are hereby incorporated by reference. Other downhole tools, such as drilling, coiled tubing and completions tools, may be used for performing the downhole operations.

The downhole tool of FIG. 1 is also provided with a sidewall coring tool 112 that is advanced into the sidewall 114 of the wellbore to take core samples of the formation. Examples of techniques for coring are described in U.S. patent application Ser. No. 2004/0140126, the entire contents of which is hereby incorporated by reference.

Samples collected by the downhole tool are typically stored in chambers 116. For example, fluid samples are drawn into sample chambers or bottles that are removed when the tool is retrieved to the surface. Similarly, core samples are drilled out using a coring tool having a sleeve 118 therein. The core sample and surrounding sleeve are transferred into a storage bin 120 and removed when the tool is retrieved to the surface.

Samples of other wellbore fluids, such as wellbore mud or fracturing fluids, are also sometimes collected by the downhole tool. For example, mud may be collected directly from the wellbore, from the downhole tool or from a mud pit 122 at the surface. Such fluids may be collected in a variety of containers.

FIGS. 2A-2C depict a variety of containers 200(a, b, c) with markers 206(a, b, c) used for collecting specimens, such as samples. FIG. 2A depicts a container 200a positionable in a downhole tool, such as the tool of FIG. 1, for collecting fluid samples. The sample chamber of FIG. 2A typically has an internal piston 202 for pressurizing a cavity 204 in the chamber. The sample chamber is typically inserted into the downhole tool and deployed into the wellbore. Samples are collected in the chambers and retrieved to the surface. The chambers are then removed and tested at the wellsite, or at an offsite laboratory.

The sample chamber of FIG. 2A is preferably provided with a marker 206a containing information about the container and/or sample contained therein. For example, the container may be adapted to identify the sample chamber. As shown in FIG. 2A, the marker is embedded in the sample chamber. Optionally, as described below, the marker may be readable. Additionally, the marker may be of a type that is adapted to upload additional information.

FIG. 2B is another container 200b that may be used for collecting specimens, such as samples, parts, or any other wellbore items. FIG. 2B is preferably provided with a marker 206b applied to the container. As shown in FIG. 2B, the marker is a series of grooves positioned about the container. The grooves may be etched into or applied to the container. Alternatively, the container may be made such that the grooves are defined by the container. The grooves are preferably positioned such that they are readable.

FIG. 2C depicts a container 200c for housing a core sample 208. The container of FIG. 2C is preferably a tubular sleeve that encompasses the core sample and protects it from damage. Typically, a core sample is captured in the core sleeve during the coring process and travels with the core sample to a storage bin (ie. 120 in FIG. 1). The container of FIG. 2C is preferably provided with a marker 206c that is a tag applied to the container. The marker may be applied at any location. Preferably, the marker is applied such that it is readable. In some cases, the marker may be placed such that it is protected from wellbore operations FIG. 3 shows a set 300 of containers 200c with markers 200d applied thereto. The containers of FIG. 3 are core sleeves, such as the ones shown in FIG. 2C. The set includes multiple core sleeves that are connected for use in a downhole tool. The core sleeves may be separated before insertion into the downhole tool, or during operations.

The containers 200c may be prepackaged sets of containers, perhaps shipped in a cartridge that snaps into the tool without handling of the individual containers. The samples may be shipped with the cartridge without requiring additional handling. One or more markers may be applied to one or more containers in the prepackaged set. The markers 200d as shown in FIG. 3 are etchings cut into the containers. This marker would typically be etched, engraved, or stamped onto the container, for example on the sidewall or the bottom. Preferably, the markers are positioned such that they are easily applied and/or read. The multiple markers provides a system for cataloging a series of containers, such as the coring sleeves depicted. Other containers, such as those of FIGS. 2A-2B may also be joined, collected or grouped in multiple sets.

Each of the containers depicted in FIGS. 2A-2C and 3 are provided with some form of marker. These markers may be used for identification, inventory, data capture, communication and/or other purposes. In some cases, multiple items may be placed in a single container. It may be possible to enter data such that the multiple contents are identified. Alternatively, one or more markers of one or more types may be applied to a container or group of containers.

A variety of markers may be used. As shown in FIG. 2A, the marker 200a is an RFID tag or chip embedded in the sample chamber. As shown in FIG. 2B, the marker is a series of physical grooves or bumps on the container which act as a binary indicator for mechanical switches. As shown in FIG. 2C, the marker is an ID tag, such as a bar code or magnetic strip, applied to the container. As shown in FIG. 3, the marker is an engraving etched directly to the container. One or more of these and other identification markers may be used on a variety of containers. The markers may be, for example, a serial number or other identifier positioned on the container. The marker may be located anywhere on the container, such as on the interior or exterior thereof.

Referring now to FIG. 4, a scanner 400 is preferably provided to read and/or write to a given marker, such as those depicted in FIGS. 2A-2C and 3. The scanner may be a stand alone device positionable adjacent a container and marker. As shown, the scanner is a stand alone laser scanner positioned adjacent a container 200c to read the bar code 206c. The scanner may be located on or off site, uphole and/or downhole. The scanner is also preferably adapted to scan data from the marker without requiring removal of the container and/or maker from the downhole tool.

The scanner may optionally be operatively connected to the downhole tool, preferably in a position adjacent the container. The scanner may be positioned in the tool to directly contact a sample in the downhole tool. In this implementation, the tool can log marker information before, during or after a sample is taken. This operation may be automated to provide direct entry of data relating to a specific sample and/or the wellbore operation. The marker may then contain a variety of data relating to the container, sample, wellbore, formation and more.

A variety of markers may be used in connection with various containers. The marker may be used for identification purposes, for example a serial number that is manually or automatically readable. The marker may also be adapted to receive and/or store data. Information about the container, such as location, may be recorded to the marker and uploaded to a processor. The information may then be transmitted, processed and analyzed using software. Assuming, for example, multiple core samples were to be taken in a run, the multiple separate serial numbers would be entered into the control computer, which would then automatically keep a log of which core was placed in which container. This log would allow all data taken during the coring operation to be related directly to a core sample. In addition, it would be possible to store other information directly in the marker, such as characteristics of the sample as measured by the downhole tool, or even comments or remarks ort other data sent from the surface acquisition unit to the downhole tool.

FIG. 2A depicts a marker embedded in can. In this implementation, a small radio frequency identification (RFID) tag, magnetic strip or chip may be embedded somewhere in the can. An RFID tag uses an electronic circuit or tag embedded in the sample bottle to store information. The tag is also capable of recording new data. Examples of RFID technology may be found in the document entitled *Radio Frequency Identification (RFID) White Paper*, by Accenture (Nov. 16, 2001) available at the following website: http://www.accenture.com/xd/xd.asp?it=enweb&xd=services%5Ctechnology%5Cvision%5Csil_val.xml.

When using an RFID tag as a marker, the RFID tag may be read using a scanner, such as the one in FIG. 4. A scanner for an RFID tag is a device that communicates wirelessly to the tag (both the scanner and the tag may be provided with antennas). Such a scanner may be adapted for use in downhole operations. The RF signal may be particularly useful in wellbore operations where it may be necessary to scan through a small amount of mud. RFID tags may be used in conjunction with software applications, run for instance in a personal computer, to initiate the communication between the reader and the tag to read the data or write new information.

Like the RFID tag, a magnetic strip, or series of magnetic strips, may be used to identify a container. The magnetic strip could be a classical magnetic strip, such as found on a credit card. Alternatively, for a more robust downhole design with less information storage capability, a series of simple magnetized rings or lines on the container could be read as the container moves through a hall effect or other magnetic sensor. These types of sensors are adaptable to high temperature environments like the wellbore, and could be sealed in oil and placed in proximity to the container's magnetic strips.

The marker of FIG. 2B as depicted is a bar code. This marker may include information, such as a text serial ID, in the form of a bar code. The bar code may be read manually, or scanned automatically using an optical scanner. An uphole scanner, such as the scanner of FIG. 4 may be used to log the serial numbers as they are inserted into the tool.

As shown in FIG. 2C, physical grooves or bumps may be used as a marker. Small physical features on the can, such as bumps or grooves, can be used and read by a scanner, such as a profilometer or other mechanical switch.

Figure 5:
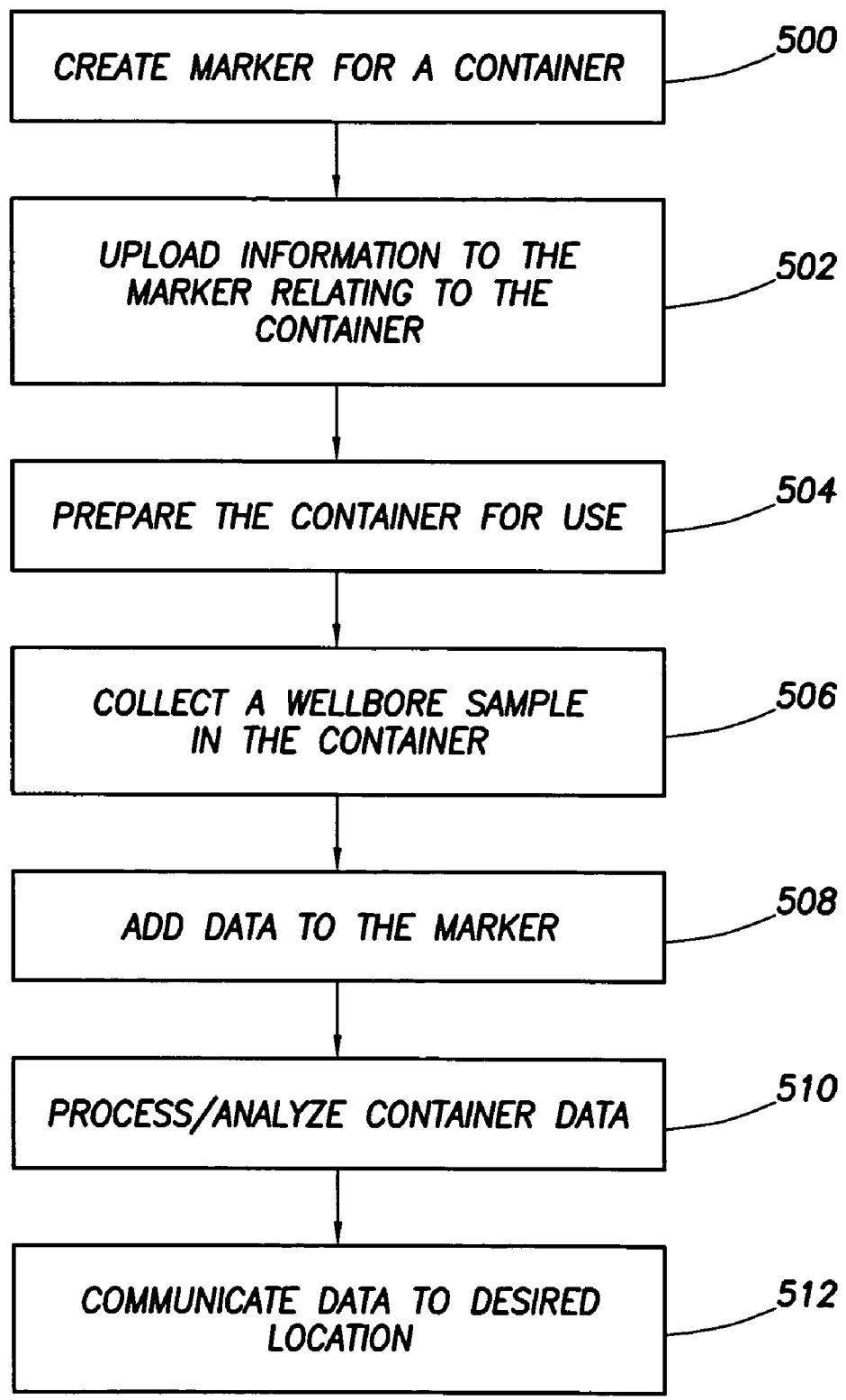
FIG. 5 is flow chart of a method of marking a container of a downhole tool.

Processors may be used to manipulate the data associated with a given container and/or marker. Software that controls the communication between die scanners and the markers may be used to store information, such as fluid property measurements and sampling information, in the marker while the container is capturing a sample downhole. Software may also be used to facilitate entering the information contained in die marker into an archive created for that particular sample. A web-based database can be used to access information in real time. FIG. 5 depicts an inventory system for marking, identifying, and processing data relating to wellbore samples collected in containers, With this method, a marker is created for a given container 500. This may be any of the markers described herein. Information relating to the container is associated with the marker 502. For example, a marker with a serial number, bottle type and date of preparation may be inserted in a clean bottle in the fluids laboratory. Other data that can be used may include, for example, tool identification, maintenance schedules, jobs completed, wellbore information, tool measurements, etc. The information may be contained in the marker, or associated processing equipment catalogued by a marker identifier.

The container may then be placed into use 504. This may require transporting the container to the wellsite for use. The markers may be scanned for information prior to insertion into the tool. Additional information may be applied to the marker prior to use.

The container is preferably used to take samples 506. However, the container may also be used to store specimens, such as parts or other wellbore equipment. The bottles may be inserted in a sampling tool and deployed downhole to capture a sample, or used at the surface to collect a specimen.

Data relating to the sample may be added to the marker 508. Readers may be used to communicate information associated with the container and relate it to information known from the marker. For example, data collected by a sample chamber may be collected with the scanned information, such as serial numbers, bottle types and positions in the tool. Also, as described above, data at the lab and/or wellsite may be added to the marker during processing.

During sampling, when a container is activated, a data acquisition system may also be activated to send information to the scanner. The scanner may then be used to write data to the marker of the active container. Data to be stored may include, for example: date of sampling, wellbore name, client, bottle opening time, depth, bottle opening pressure, bottle closing pressure, temperature, etc. Other measurements data collected during the wellbore operation may be also stored in the marker. Such data may be reproduced in the lab for comparison in order to validate the sample. Examples of data that may be collected includes, for example fluorescence intensity, color, density, viscosity, optical spectrum, pH, hydrogen sulfide content, GOR and fluid composition.

Information about the container and/or its specimen may be processed and/or analyzed 510. A data acquisition system may be used to manipulate the information. Comparisons of various samples and other data analysis may be performed using such a system. The information in the marker may be loaded into an Internet database. Information may be read from the marker and results stored in the marker and/or in an on-line database archive. If the sample is transported to a laboratory, markers may be scanned to identify the container and/or sample. For each analysis performed, the results (as well as other information) may be stored in a database archive created for that sample.

Information may be collected and communicated as necessary 512. Information may be transferred to the surface automatically, or the tool may be retrieved and the information downloaded or transferred at the surface.

At the surface, if a sample is transferred from one container to a different container, the scanner may scan the marker, and copy this information into the marker of the new bottle. The containers may be cleaned and conditioned for a new sample. Information in the markers may be reused, or cleared for new information.

While certain steps are depicted in FIG. 5, it will be appreciated by one of skill in the art that the steps are not necessarily in order, certain steps may be performed more than once or not at all, and that additional steps may also be performed in conjunction with the method described. For example, information from the marker may be uploaded to and/or downloaded from the marker one or more times as needed.

The details of certain arrangements and components of the plug(s) and associated system described above, as well as alternatives for such arrangements and components would be known to persons skilled in the art and found in various other patents and printed publications, such as, those discussed herein. Moreover, the particular arrangement and components of the downhole fluid sampling system may vary depending upon factors in each particular design, or use, situation. Thus, neither the fluid sampling system nor the present invention are limited to the above described arrangements and components, and may include any suitable components and arrangement. For example, various flow lines, pump placement and valving may be adjusted to provide for a variety of configurations. Similarly, the arrangement and components of the downhole tool and the probe assembly may vary depending upon factors in each particular design, or use, situation. The above description of exemplary components and environments of the tool with which the probe assembly and other aspects of the present invention may be used is provided for illustrative purposes only and is not limiting upon the present invention.

The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A marking system for a well site sample, comprising:
    at least one container for collecting the well site sample;
    at least one marker applied to the at least one container, the at least one marker having an identifier associated therewith; and
    a scanner positioned in a downhole tool for reading the at least one marker.

2. The marking system of claim 1 wherein the at least one marker is one of an etching, an RFID tag, a magnetic strip, a bar code, a set of grooves and combinations thereof.

3. The marking system of claim 1 further comprising a processor for processing data associated with the at least one marker.

4. The marking system of claim 1 wherein the sample is one of a core sample, a wellbore fluid sample, a formation fluid sample, a frac fluid sample and combinations thereof.

5. The marking system of claim 1 wherein the scanner is for writing to the at least one marker.

6. The marking system of claim 1 wherein the at least one marker is embedded in the at least one container.

7. The marking system of claim 1 wherein the at least one marker is etched into the at least one container.

8. The marking system of claim 1 wherein the at least one marker has circuitry for storing data.

9. The marking system of claim 1 wherein the identifier is a serial number.

10. A method of processing downhole data for a well site sample, comprising:
    creating an at least one marker for an at least one container;
    uploading background data relating to the at least one container to the at least one marker using a scanner positioned in a downhole tool;
    collecting a well site sample in the at least one container; and
    downloading the data to a surface computer.

11. The method of claim 10 further comprising uploading wellbore data relating to the well site sample to the at least one marker.

12. The method of claim 11 wherein the step of uploading wellbore data comprises writing well site data to the at least one marker.

13. The method of claim 10 further comprising uploading laboratory data relating to the well site sample to the at least one marker.

14. The method of claim 13 wherein the step of uploading laboratory data comprises writing laboratory data to the at least one marker.

15. The method of claim 10 further comprising processing the data.

16. The method of claim 10 further comprising analyzing the data.

17. The method of claim 10 wherein the step of creating an at least one marker comprises applying an at least one marker to the at least one container.

18. The method of claim 10 wherein the step of creating an at least one marker comprises etching an at least one marker onto the at least one container.

19. The method of claim 10 wherein the step of creating an at least one marker comprises creating grooves on the at least one container.

20. The method of claim 10 wherein the step of collecting comprises collecting a fluid sample in the at least one container.

21. The method of claim 10 wherein the step of collecting comprises collecting a core sample in the at least one container.

22. The method of claim 10 wherein the step of collecting comprises collecting a well site sample in the at least one container.

23. The method of claim 10 wherein the step of uploading background data comprises writing background data to the at least one marker.

24. The method of claim 10 wherein the step of downloading comprises reading the data from the at least one marker.

25. The method of claim 10 further comprising transferring the well site sample from the at least one container to a second container having a second marker and transferring data from the at least one marker to the second marker.

26. The method of claim 10 wherein the step of uploading is performed automatically.

27. The method of claim 10 wherein the step of downloading is performed automatically.

28. A marking system for a well site sample, comprising:
at least one container positioned in a downhole tool for collecting the well site sample;
at least one radio frequency identification tag applied to the at least one container, the at least one radio frequency identification tag having an identifier associated therewith; and
a scanner adapted to read the at least one radio frequency identification tag.

29. The marking system of claim 28 wherein the scanner is further adapted to write to the at least one radio frequency identification tag.

30. The marking system of claim 29 wherein the at least one radio frequency identification tag has circuitry adapted to store data.

* * * * *